United States Patent [19]

Kikuchi et al.

[11] Patent Number: 4,687,661

[45] Date of Patent: Aug. 18, 1987

[54] METHOD FOR PRODUCING LIPOSOMES

[75] Inventors: Hiroshi Kikuchi; Hitoshi Yamauchi, both of Tokyo, Japan

[73] Assignee: Daiichi Seiyaku Co., Ltd., Tokyo, Japan

[21] Appl. No.: 625,078

[22] Filed: Jun. 27, 1984

[30] Foreign Application Priority Data

Jun. 29, 1983 [JP] Japan ............................. 58-118006

[51] Int. Cl.$^4$ ..................... A61K 31/70; A61K 9/10; A61K 39/02
[52] U.S. Cl. ..................................................... 424/38
[58] Field of Search ........................................ 424/38

[56] References Cited

U.S. PATENT DOCUMENTS

| 3,640,892 | 2/1972 | Purcell | 424/38 |
| 4,217,344 | 8/1980 | Vanlerberghe et al. | 424/38 |
| 4,235,871 | 11/1980 | Papahadjopoulos et al. | 424/38 |
| 4,298,594 | 11/1981 | Sears et al. | 424/38 |
| 4,356,167 | 10/1982 | Kelly | 424/38 |
| 4,389,330 | 6/1983 | Tice et al. | 424/38 |
| 4,460,577 | 7/1984 | Moro et al. | 424/38 |
| 4,532,089 | 7/1985 | Mac Donald | 424/38 |

FOREIGN PATENT DOCUMENTS 3335701 4/1984 Fed. Rep. of Germany ........ 424/38

OTHER PUBLICATIONS

Chemical Abstracts, vol. 78, No. 25, Jun. 25, 1973, abstract 78:155690j.
Chemical Abstracts, vol. 87, No. 22, Nov. 28, 1977, abstract 87:172885e.
Chemical Abstracts, vol. 91, No. 13, Sep. 24, 1979, abstract 91:104622z.
Chemical Abstracts, vol. 92, No. 22, Jun. 2, 1980, abstract 92:185939d.
Chemical Abstracts, vol. 94, No. 9, Mar. 2, 1981, abstract 94:61116e.

Primary Examiner—Ronald W. Griffin
Attorney, Agent, or Firm—Sughrue, Mion, Zinn, Macpeak & Seas

[57] ABSTRACT

A method for producing liposomes which comprises mixing liposome membrane components with a water-soluble non-volatile solvent and, then, dispersing the mixture in an aqueous medium. The pharmaceutically acceptable liposome preparation as a drug delivery system can thus be produced with efficiency on an industrial scale.

13 Claims, No Drawings

METHOD FOR PRODUCING LIPOSOMES

FIELD OF THE INVENTION

The present invention relates to a novel method for producing liposomes.

DESCRIPTION OF THE PRIOR ART

While the liposomes which are lipid vesicles have been used widely as a model membrane system, they have recently been utilized in various applications related to a drug delivery system. The liposomes can be roughly classified into three types, viz., multilamellar vesicles (MLV), large unilamellar vesicles (LUV) and small unilamellar vesicles (SUV), and various kinds of techniques have been proposed for the preparation of these types of liposomes (*Annual Review of Biophysics and Bioengineering,* 9, 467, 1980). However, these techniques are useful for the preparation of liposomes on a test tube or flask scale and connot be applied industrially. The factors inadequate for their use in industrial production are as follows.

(1) All these methods involve the use of volatile organic solvents harmful to human health, such as chloroform, benzene or diethyl ether, for dissolution of lipids, with the result that they raise safety problems in technical procedure and human health.

(2) For the same reason as above, the organic solvent tends to remain in the final preparation.

(3) In the vortexing method (*Journal of Molecular Biology,* 13, 238, 1965) which is a typical prior art technology, a thin film has to be formed on glass wall but this process cannot be easily carried out on a large scale of production. Thus, although various clinical applications on liposomes have been studied by many workers, no commercial liposome preparation has been on the market as yet. Recently, some industrial methods for producing liposomes have been proposed as disclosed in, for example, Japanese patent application (OPI) Nos. 136514/82 and 171915/82 (the term "OPI" as used herein refers to a "published unexamined Japanese patent application"). These methods describe improved modifications of the so-called detergent method (*Biochimica et Biophysica Acta,* 323, 547, 1973), and ethanol injection method (*Biochimica et Biophysica Acta,* 298, 1015, 1973) or ether infusion method (*Biochimica et Biophysica Acta,* 443, 629, 1976), respectively. The former method has disadvantage that the ethanol used as a solvent must be removed under reduced pressure and the detergent used as a lipid solubilizer must also be removed by dialysis or gel filtration. The latter method has also disadvantage that the organic solvent used such as ethanol or hexane must be removed from the final preparation by heating or other procedures and that the speed of injecting the organic solvent into the aqueous medium must be critically controlled with greatest possible care. Thus, none of the known methods is fully satisfactory for the industrial production of liposomes.

Under the foregoing circumstances, the present inventors conducted studies for the development of a new industrially useful method for producing liposomes and completed the present invention. That is, the present inventors have found that homogeneous liposomes can be obtained with ease and good reproducibility, when membrane components forming liposomes are dissolved or swollen in a water-soluble and physiologically acceptable non-volatile organic solvent and the resulting mixture is futher mixed and stirred with an aqueous medium.

SUMMARY OF THE INVENTION

The present invention is characterized in that an organic solvent which is not only water-soluble but harmless to health even if it remains in the final preparation to be administered into the human body is used as a solvent for the membrane components. Moreover, in accordance with this invention, any special equipment or procedure is not required for a large scale of production of liposomes. Therefore, the above-described factors inadequate for industrial production of liposomes have thus been completely obviated and solved.

DETAILED DESCRIPTION OF THE INVENTION

This invention relates to a method for producing liposomes which comprises mixing membrane components with a water-soluble non-volatile organic solvent and dispersing the mixture in an aqueous medium.

Examples of membrane components used in the present invention include phospholipids such as phosphatidylcholine, phosphatidylethanolamine, phosphatidylserine, phosphatidylinositol, lysophosphatidylcholine, sphingomyelin, egg yolk lecithin, soybean lecithin, etc., various glycolipids, dialkyl-type synthetic surfactants, etc. These membrane components may be used alone or in combination. The above components may contain, as auxiliary materials, membrane stabilizers such as cholesterol, cholestanol, etc., charge modifiers such as dicetyl phosphate, phosphatidic acid, ganglioside, stearylamine or the like, and antioxidants such as α-tocopherol or the like. The proportions of these auxiliary materials to the above-described membrane components are not critical. However, a preferred proportion of membrane stabilizers is about 0 to about 2 parts by weight per part by weight of the membrane components, and that of charge modifiers is about 0.1 part by weight per part by weight of the membrane components.

The water-soluble, non-volatile organic solvent used in the present invention incudes, for example, polyhydric alcohols such as glycerin, polyglycerin, propylene glycol, polypropylene glycol, ethylene glycol, triethylene glycol, polyethylene glycol, diethylene glycol monoethyl ether, 1,3-butylene glycol, maltitol, etc., glycerin esters such as monoacetin, diacetin, glycerophosphoric acid, etc., benzyl alcohol and so on. These organic solvents may be used alone or in combination. The proportion of such water-soluble organic solvents is preferably about 1 to about 100 parts by weight per part by weight of the membrane components and about 0.001 to about 2 parts by weight per part by weight of the aqueous medium.

The aqueous medium is preferably water, a physiological saline solution, a buffer solution or an aqueous carbohydrate solution, or a mixture thereof. The term "dissolved or swollen" as used herein means that the membrane components are solvated or in free admixture with the organic solvent at the molecular level. The mixture thus obtained may be a clear liquid or paste, an opaque paste or gel, or a mixture thereof. The procedure for preparing such a solvated or free mixture state will hereafter be referred to simply as "mixing". Generally, the membrane materials other than the sterols can be easily mixed with the water-soluble organic solvents by a procedure such as warming.

Thus, the membrane materials other than sterols can be easily mixed with the organic solvent by warming the mixture to a temperature up to 70° to 90° C. while stirring. When sterols are used, it is preferred to pre-warm the organic solvent to a melting point of the sterols and mix the sterols with the solvent, followed by adding other membrane materials to the mixture at a temperature of 70° to 90° C. It is of course possible to mix each of the membrane materials respectively with the organic solvent and finally combine the mixtures. The mixture thus obtained is then dispersed in an aqueous medium to form liposomes.

In order to encapsulate a drug into the liposomes, it is sufficient to mix the organic solvent containing the membrane materials with an aqueous medium containing the drug. While the mixing procedure is optional, the following considerations should be taken.

(a) It is more efficient to conduct mixing at a temperature not lower than the phase transition temperature (Tc) of the lipid. It is, therefore, preferred to pre-warm both the organic solvent containing membrane components and the aqueous medium containing the drugs to a temperature not lower than the phase transition temperature (Tc).

(b) When the organic solvent containing membrane components is a clear liquid or paste, the resulting liposomes tend to become relatively small particle size.

(c) When the organic solvent containing membrane components is an opaque paste or solid, the resulting liposomes tend to become relatively large particle size.

(d) The particle size of the obtained liposomes varies depending on the type of mixer employed. Thus, when a comparatively mild mixing machine such as a propeller mixer is employed, the liposomes tend to become relatively large particle size. When a mixing machine having a high shearing force such as a homomixer is used, liposomes tend to become small particle size. To produce liposomes of smaller particle size, an ultrasonic emulsifer or a high-pressure emulsifier can be employed. Moreover, for the purpose fo controlling the particle size distribution of liposomes, it is possible to use the ultrafiltration method, for example, a polycarbonate membrane filter.

(e) In order to improve the efficiency of drug encapsulation into the liposomes having a specific composition, it is preferred that the drug is dissolved in an aqueous medium as small volume as possible, that the resulting solution is mixed with the organic solvent containing membrane components, and that the whole mixture is diluted with the balance of aqueous medium.

There is no limitation on the drugs that can be encapsulated into the liposomes according to the present invention. For example, antitumor drugs such as cytosine arabinoside, methotrexate, etc,. antibiotics such as penicillin G, gramicidin S, etc,. proteins such as insulin, interferons, glucoamylase, etc., polysaccharides such as dextran, etc., nucleic acids such as DNA and RNA, vitamins such as vitamin A, etc., and other general drugs such as sodium salicylate, chlorophyll, chlorhexidine acetate, acetaminophen, etc., can be successfully employed. As described above, these drugs are generally used after dissolution in aqueous medium but when the drug is a lipophilic or lipid-soluble component such as chlorophyll, gramicidin S, vitamin A, etc., it is more efficient to mix it with the membrane materials in a water-soluble, non-volatile organic solvent such as concentrated glycerin, propylene glycol or the like. When the drug is water-soluble and miscible with a water-soluble organic solvent, for example, in the case of chlorhexidine acetate, acetaminophen, etc., it is more efficient to mix it with the water-soluble organic solvent together with the membrane materials.

In the above manner, drug-encapsulated liposome preparations of uniform particle size can be produced with good reproducibility and in large quantities. The liposome preparation can be used as it is, but the drug not encapsulated into the liposomes may be removed by such techniques as dialysis, gel filtration, centrifugation, etc.

In addition to the above-described advantages, the method of the present invention has the following advantages.

(1) The organic solvent used in the present invention can also serve as isotonizing agents.

(2) The organic solvent used in the present invention serves as dispersants as well and prevents coagulation or sedimentation of the vesicles thereby enhancing the stability of the liposome preparations.

(3) The organic solvent used in the present invention improves the stability of the liposome preparations against freezing, thawing, etc.

The present invention is further illustrated by the following examples, but the invention is not limited thereto.

EXAMPLE 1

Concentrated glycerin (9.4 g) was heated to 94° C. and 2.2 g of completely hydrogenated pure egg yolk lecithin (IV=1, phospholipid content: 99% or more, Tc=45°–60° C., Tmax=52° C.) and 164 mg of dicetyl phosphate were added. The mixture was stirred to effect uniform swelling. The mixture was then stirred on a water bath at 60° C., whereupon it became a white, homogeneous paste. To this paste was added 300 ml of a 0.5% aqueous solution of sodium salicylate pre-warmed to 60° C. and the mixture was allowed to stand at 60° C. for 3 minutes so as to cause the paste to swell. Finally, this mixture was stirred in a homomixer at 60° C. for 3 minutes, after which it was cooled to room temperature. The above procedure yielded a milk white, sodium salicylate-encapsulating liposome suspension. An 8 ml portion of the above liposome suspension was put in a UCC tubular cellophan dialysis bag and dialyzed against 1 l of a physiological saline solution (at 5° C., 1 l×1 hour×6 times) to remove the sodium salicylate not encapsulated into the liposomes. Then, the sodium salicylate encapsulated within the liposomes was assayed by extraction into water by the routine oil/water distribution technique. The encapsulation efficiency was found to be 10.0%.

Examination of the above liposome suspension under an optical microscope (the broad-field optical microscope made by Nippon Kogaku) showed that the vesicles were spherical and uniformly sized, the particle size being approximately 1 μm.

EXAMPLE 2

Propylene glycol (7.2 g) was heated to 92° C. on a water bath, and 8.9 g of partially hydrogenated pure egg yolk lecithin (IV=20, phospholipid content: 99% or more, Tc=5°–50° C., Tmax=35° C.) and 320 mg of stearylamine were added and dissolved to give a clear liquid. When allowed to stand at 60° C., it remained colorless and clear. To this colorless, clear solution was added 300 ml of a 1% aqueous solution of dextran T 40 prewarmed to 55° C. and the mixture was stirred in a propeller mixer at 50° to 55° C. for 3 minutes, after which it was cooled to room temperature. The above procedure yielded a milk white, dextran T 40-encapsulating liposome suspension.

A 1 ml portion of the above suspension was applied to gel filtration on Sephalose CL-4B (2.2 cm diameter × 42 cm, saline, at 5° C.) to remove the dextran T 40 not encapsulated into the liposomes. Then, dextran T 40 in the liposome fraction was extracted into water by the routine oil/water distribution technique. The encapsulation efficiency was found to be 14.3%.

Examination of the gel filtration liposome fraction revealed that the vesicles were spherical and uniform in size ranging from 0.5 to 1 $\mu$m.

EXAMPLE 3

The procedure of Example 2 was repeated except that a concentrated aqueous solution of dextran T 40 was first mixed with the membrane components and, then, stirred with an additional amount of water. Thus, as in Example 2, 7.2 g of propylene glycol, 8.9 g of partially hydrogenated egg yolk lecithin and 320 mg of stearylamine were used to prepare a colorless, clear liquid. Separately, 3 g of dextran T 40 was dissolved in 40 ml of water and added to the above colorless, clear liquid and sirred at 60° C., whereupon a white viscous liquid was obtained. This viscous liquid was diluted with 260 ml of water pre-warmed to 55° C. and the mixture was stirred in a propeller mixer for 3 minutes, after which it was cooled to room temperature. The above procedure provided a milk white, dextran T 40-encapsulating liposome suspension.

A 1 ml portion of the above suspension was applied to gel filtration in the same manner as Example 2. The encapsulation efficiency was 19.2%.

EXAMPLE 4

The procedure of Examples 2 and 3 was repeated except that dextran T 40 was used in a still higher concentration. Thus, 3 g of dextran T 40 was dissolved in 6 ml of water and added to a colorless, clear membrane component liquid similar to those prepared in Examples 2 and 3 at 60° C. to give a white paste. To this paste was added 294 ml of water pre-warmed to 55° C. and the mixture was stirred in a propeller mixer for 3 minutes, after which it was cooled to room temperature. The above procedure provided a milk white liposome suspension similar to that obtained in Example 3.

A 1 ml portion of the above suspension was assayed by gel filtration. The encapsulation efficiency was 33.5%.

EXAMPLE 5

Propylene glycol (3.6 g) was heated to 160° C. and 2.3 g of cholesterol was added. The mixture was agitated in a vortex mixer to dissolve the cholesterol in propylene glycol and the solution was allowed to stand at 60° C. so as to swell and solidify. Separately, 3.6 g of propylene glycol was taken and heated to 90° C. on a water bath, followed by addition of 4.4 g of completely hydrogenated egg yolk lecithin and 330 mg of dicetyl phosphate. The mixture was agitated in a vortex mixer and the resulting solution was allowed to stand at 60° C.

The above two preparations were combined and 300 ml of a 0.5% aqueous solution of sodium benzoate pre-warmed to 65° C. was quickly added. The mixture was stirred in a homomixer at 60° to 65° C. for 3 minutes, after which it was cooled to room temperature. The above procedure provided a milk white, sodium benzoate-encapsulating liposome suspension.

The encapsulation efficiency of sodium benzoate in the above suspension was determined by the same dialysis assay as described in Example 1. The encapsulation efficiency was 11.4%.

Examination of this liposome suspension under a broad-field optical microscope in the same manner as Example 2 revealed that the vesicles therein were spherical and uniform in size ranging from 1 to a few $\mu$m. However, the larger vesicles were onion-like in structure.

EXMAPLE 6

Propylene glycol (7.2 g) was heated to 160° C. and 970 mg of cholesterol was added thereto so as to give a clear solution. Then, 4.4 g of partially hydrogenated egg yolk lecithin and 330 mg of dicetyl phosphate were added and dissolved under stirring to give a clear solution. This was put in a water bath at 92° C. and while the membrane components remained dissolved in propylene glycol, 300 ml of a 0.5% aqueous solution of sodium benzoate pre-warmed to 55° C. was quickly added and stirred in a homomixer at 50° to 55° C. for 3 minutes, at the end of which time it was cooled to room temperature. The above procedure provided a milk white, sodium benzoate-encapsulating liposome suspension.

A 0.5 ml portion of the above suspension was applied to gel filtration on Sepahdex G-50 (1 cm diameter × 18 cm, saline, at 5° C.) to remove the sodium benzoate not encapsulated in the liposomes. Then, sodium benzoate in the liposome fraction was assayed by the routine method. The encapsulation efficiency was 3.9%.

Examination of the liposome fraction revealed that the vesicles were uniform in size ranging from 0.5 $\mu$m and less.

EXAMPLE 7

The procedure of Example 6 was repeated except that 2.3 g of cholesterol was employed. The encapsulation efficiency was 5.9%. Examination of the gel filtration liposome fraction under a broad-field optical microscope revealed that the particle size of the liposome was also 0.5 $\mu$m or less.

EXAMPLE 8

Concentrated glycerin (9.4 g) was heated to 160° C. and 1.47 g of cholesterol was added and stirred until the latter was well swollen. Thereafter, 6.7 g of completely hydrogenated egg yolk lecithin and 490 mg of dicetyl phosphate were added and thoroughly kneaded. This preparation was a colorless, translucent paste at 160° C. but changed to a white, opaque paste when cooled to 60° C. To this paste was added 300 ml of a 0.5% aqueous solution of sodium salicylate pre-warmed to 65° C. and the mixture was stirred in a homomixer at 60° to 65° C. for 3 minutes, at the end of which time it was cooled to room temperature. The above procedure provided a milk white, sodium salicylate-encapsulating liposome suspension.

A 0.5 ml portion of the above suspension was applied to gel filtration (at room temperature) as in Example 6.

The encapsulation efficiency of sodium salicylate in the liposome was 17.0%.

Examination of the liposome fraction under a broad-field optical microscope revealed that the mean particle size of the liposomes was about 1 μm, there being sporadically observed comparatively large vesicles. These larger vesicles were onion-like in structure.

EXAMPLE 9

The procedure of Example 1 was repeated except that L-α-dipalmitoylphosphatidylcholine (purity 98%, Tc=41° C.) was used in lieu of completely hydrogenated pure egg yolk lecithin and the stirring was conducted at 40° to 45° C. The procedure provided a milk white, sodium salicylate-encapsulating liposome suspension.

The encapsulation efficiency of sodium salicylate in the liposome was determined by dialysis in the same manner as Example 1. The encapsulation efficiency was 13.3%.

Examination of the liposomes under a broad-field optical microscope revealed that the vesicles were spherical and uniform in size ranging from 1 to a view μm.

While the inventoin has been described in detail and with reference to specific embodiments thereof, it will be apparent to one skilled in the art that various changes and modifications can be made therein without departing from the spirit and scope thereof.

What is claimed is:

1. A method for producing liposomes which comprises:
   (A) mixing liposome membrane components with a water-soluble, physiologically acceptable, non-volatile organic solvent which is in a liquid state at a temperature of from 70°–90° C., wherein said water-soluble, physiologically acceptable, non-volatile organic solvent is at least one member selected from the group consisting of glycerin, polyglycerin, propylene glycol, polypropylene glycol, ethylene glycol, triethylene glycol, polyethylene glycol, diethylene glycol monoethyl ether, 1,3-butylene glycol, maltitol, glycerin esters and benzyl alcohol, and
   (B) dispersing the resulting mixture in an aqueous medium.

2. A method for producing liposomes as claimed in claim 1, wherein said water-soluble non-volatile organic solvent is used in a proportion of about 1 to about 100 parts by weight per part by weight of said membrane components and about 0.001 to about 2 parts by weight per part by weight of said aqueous medium.

3. A method for producing liposomes as claimed in claim 1, wherein said membrane components are selected from the group consisting of phospholipids, glycolipids and dialkyl-type synthetic surfactants.

4. A method for producing liposomes as claimed in claim 3, wherein said membrane components further contain at least one of membrane stabilizers, charge modifiers and antioxidants.

5. A method for producing liposomes as claimed in claim 4, wherein said membrane stabilizers are used in a proportion of about 0 to about 2 parts by weight per part by weight of the membrane components.

6. A method for producing liposomes as claimed in claim 4, wherein said charge modifiers are used in a proportion of about 0.1 part by weight per part by weight of the membrane components.

7. A method for producing liposomes as claimed in claim 1 or 3, wherein said membrane components are mixed with said water-soluble non-volatile organic solvent at a temperature of 70° to 90° C.

8. A method for producing liposomes as claimed in claim 4, wherein said membrane stabilizer is a sterol.

9. A method of producing liposomes as claimed in claim 8, wherein said sterol is mixed with said water-soluble non-volatile organic solvent at a temperature not lower than the melting point of the sterol.

10. A method for producing a liposome preparation which comprises:
    (A) mixing liposome membrane components with a water-soluble, physiologically acceptable, non-volatile organic solvent which is in a liquid state at a temperature of from 70°–90° C., wherein said water-soluble, physiologically acceptable, non-volatile organic solvent is at least on member selected from the group consisting of glycerin, polyglycerin, propylene glycol, polypropylene glycol, ethylene glycol, triethylene glycol, polyethylene glycol, diethylene glycol monoethyl ether, 1,3-butylene glycol, maltitol, glycerin esters and benzyl alcohol,
    (B) dispersing the resulting mixture in an aqueous medium, and
    (C) encapsulating a drug into the resulting liposomes.

11. A method for producing a liposome preparation as claimed in claim 10, wherein a water-soluble drug is added to the aqueous medium and said water-soluble non-volatile organic solvent containing said membrane component is mixed with said aqueous medium.

12. A method for producing a liposome preparation as claimed in claim 10, wherein a lipid-soluble drug is added to said water-soluble non-volatile solvent and is mixed with said aqueous medium.

13. A method for producing a liposome preparation as claimed in claim 10, wherein a drug miscible with said water-soluble organic solvent is added to said water-soluble non-volatile organic solvent and is mixed with said aqueous medium.

* * * * *